United States Patent [19]

Pannwitz

[11] Patent Number: 4,946,649
[45] Date of Patent: Aug. 7, 1990

[54] COLORIMETRIC GAS DIFFUSION TESTING TUBE

[75] Inventor: Karl-Heinz Pannwitz, Lübeck, Fed. Rep. of Germany

[73] Assignee: Drägerwerk Aktiengesellschaft, Lübeck, Fed. Rep. of Germany

[21] Appl. No.: 824,191

[22] Filed: Jan. 30, 1986

[30] Foreign Application Priority Data

Jan. 31, 1985 [DE] Fed. Rep. of Germany ....... 3503234

[51] Int. Cl.⁵ ............................................. G01N 31/22
[52] U.S. Cl. ...................................... 422/60; 422/83; 422/86; 422/88; 436/126; 436/902
[58] Field of Search ..................... 422/60, 86, 88, 83; 436/126, 902

[56] References Cited

U.S. PATENT DOCUMENTS

| | | | |
|---|---|---|---|
| 3,312,527 | 4/1967 | McConnaughey | 422/86 X |
| 3,507,623 | 4/1970 | McConnaughey | 42/86 |
| 4,159,304 | 6/1979 | Shono | 422/86 X |
| 4,271,125 | 6/1981 | Leichnitz | 422/86 |
| 4,528,160 | 7/1985 | Eckstein et al. | 422/102 X |
| 4,595,011 | 7/1986 | Phillips | 204/403 X |

FOREIGN PATENT DOCUMENTS 1498909  4/1969  Fed. Rep. of Germany .
1075054  7/1967  United Kingdom .

OTHER PUBLICATIONS

Detector Tube Handbook, Drägerwerks, Germany, (1979), 4th Ed., pp. 8–25, 150–153.

Primary Examiner—Robert J. Warden
Assistant Examiner—Jill Johnston
Attorney, Agent, or Firm—Walter Ottesen

[57] ABSTRACT

A colorimetric gas diffusion testing tube is disclosed that is to be opened at one end and that contains a granular indicator layer. The testing tube detects a gas that does not directly change the color of the indicator layer. When the tube is viewed from the end which is to be opened, the indicator layer that is adjacent the opening end is inert to the gas that is to be detected. The indicator layer is followed by a porous reagent layer for converting this gas into the substances that change the color of the indicator layer.

7 Claims, 1 Drawing Sheet

COLORIMETRIC GAS DIFFUSION TESTING TUBE

FIELD OF THE INVENTION

The invention relates to a colorimetric gas diffusion testing tube having a transparent tube that can be opened at one end. The transparent testing tube contains a porous indicator layer.

BACKGROUND OF THE INVENTION

A testing tube of this type is known from German published patent application DE-OS 14 98 909. The known testing tube is used as a colorimetric gas dosimeter which contains a granular indicator layer within a glass tube. The glass tube, which can be opened at one end, is exposed to the gaseous toxic substance that is to be detected and a recognizable change in color is caused by diffusion of the gaseous toxic substance into the porous indicator layer when there is a corresponding impregnation of the carrier material. The advancing diffusion of the toxic substance into the indicator layer is indicated by the progression of the zone of altered coloration, which accordingly provides a measure of the quantity of toxic substance in the gas that is being tested. Gases that can be detected with gas dosimeters of this type are those which produce a color reaction directly with the indicator. Among these gases are hydrogen sulfide, sulfur dioxide, nitrogen dioxide and ammonia. Vapors of organic solvents, such as trichloroethene vapors, cannot be measured with this gas dosimeter tube.

However, U.S. Pat. No. 4,271,125 discloses that testing tubes intended for quantitative analysis, for instance of metal cyanides in aerosol form, are provided with a front layer of a carrier material impregnated with sulfuric acid or phosphoric acid, which with the metal cyanides forms a substance that is then detected by means of a color reaction with an indicator layer which follows the front layer. To detect the toxic substance that is to be investigated, a defined quantity of test air is passed through this known testing tube by means of a suction device, so that in the direction of the flow of testing air, the reagent layer must be arranged ahead of the indicator layer. If the air sample that is passed through the tube reaches the reagent layer first, then the toxic substance that is to be measured is converted into other reaction products, some of them gaseous. As the air sample continues to be aspirated through the tube, the gaseous reaction products leave the reagent layer and enter the following indicator layer, where they are converted into a colored reaction product and form a colored zone; at a given sample volume, the length of this colored zone is a function of the concentration of the toxic substance that is to be detected.

If the order in which the reagent layer and the indicator layer are arranged in the known through-flow testing tube were adopted for the known gas diffusion testing tube that can be opened at only one end, there would be a partial back diffusion of reaction products from the reagent layer to the opening of the gas diffusion testing tube, which would not produce a color change in the indicator layer that would be a function of the actual concentration. The back-diffused reaction products make no contribution at all to the color change in the indicator layer.

SUMMARY OF THE INVENTION

It is an object of the invention to provide a colorimetric gas-diffusion testing tube of the type described above which can detect gases which do not produce a direct color reaction in the indicator layer.

The colorimetric gas diffusion testing tube of the invention includes a testing tube having an indicator layer which is inert to the gas that is to be detected and this indicator layer is the first component when viewed from the end of the tube that can be opened. Next in the direction from the opening, a porous reagent layer is provided for converting the gas that is to be detected into substances that change the color of the indicator layer.

Arranging the indicator and reagent layers in the order provided by the invention assures that the reaction products, which are produced in the reagent layer and flow through the indicator layer toward the opened end of the gas diffusion testing tube because of the concentration gradient, can be converted into a colored reaction product in the indicator layer and form a colored zone the length of which corresponds to a predetermined quantity of the gas that is to be detected.

In a further advantageous embodiment of the invention, a further indicator layer may be provided following the reagent layer. As a consequence thereof, the reaction products produced in the reagent layer will pass into an indicator layer in both diffusion directions wherein they bring about a color reaction. This shortens the indication time for the quantity of toxic substance to be detected.

The indicator layer and the reagent layer can suitably be fixed in their respective positions with porous retainer elements.

The reagent layer and the indicator layer may have a conventional configuration, as known from through-flow testing tubes depending on the composition of the gas that is to be detected.

To detect trichloroethene, for instance, the carrier material of the reagent layer should be impregnated with chromium (VI) oxide and sulfuric acid, and the carrier material of the indicator layer should be impregnated with o-tolidine.

BRIEF DESCRIPTION OF THE DRAWING

The invention will now be described with reference to the drawing wherein.

DESCRIPTION OF THE PREFERRED EMBODIMENT OF THE INVENTION

Figure 1:
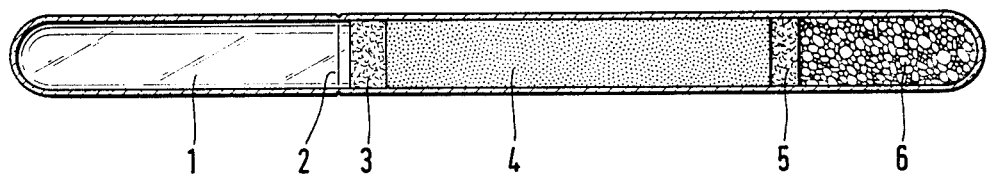
FIG. 1 is a side elevation view, in section, of a closed testing tube, according to an embodiment of the invention.
Figure 2:
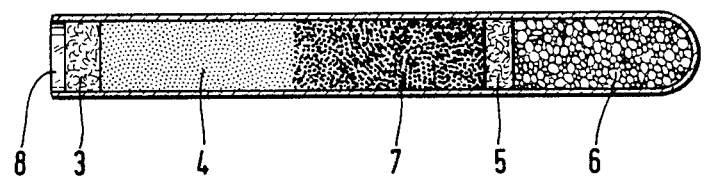
FIG. 2 is a side elevation view, in section, of an opened testing tube.
Figure 3:
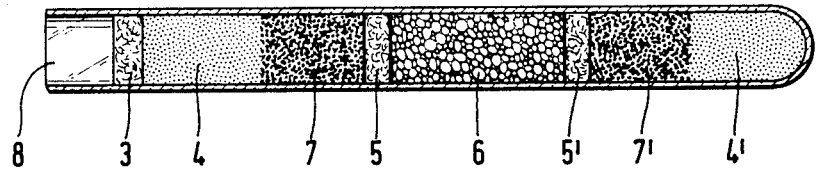
FIG. 3 is a side elevation view, in section, of a further opened test tube according to another embodiment of the invention.

The diffusion testing tube includes a transparent tube 1, preferably made of glass, which prior to being used is closed at both ends and can be opened at one end by being broken at the scoring 2. Beginning from the opening 8, the contents of the glass tube 1 are a porous plug 3, the indicator layer 4, the porous retainer element 5 and the granular reagent layer 6. With the testing tube opened, a colored zone 7 is visible within the indicator layer 4 once there has been a reaction in the reagent layer 6 of the gas that is to be detected. If another indicator layer 4' is provided in the testing tube following the reagent layer 6, then the colored zones 7, 7' can be recognized in the indicator layers 4, 4' as shown in FIG. 3.

For detecting trichloroethene vapors, for instance, using the gas diffusion testing tube according to the invention, the trichloroethene molecules diffuse into the testing tube after the glass tube 1 has been opened at the scoring 2. This diffusion occurs because of the concentration gradient between the exterior and the interior of the glass tube 1. In so doing, the trichloroethene molecules migrate through the porous plug 3, the granular indicator layer 4 and the porous retainer element 5 until they reach the reagent layer 6. Here, the chemical reaction between trichloroethene and chromium (VI) oxide takes place, and chlorine and other reaction products are released.

Since the reaction layer 6 is located at the closed end of the glass tube 1, the released chlorine diffuses in the opposite direction through the porous retainer element 5 back into the indicator layer 4. Here, the chemical reaction between chlorine and o-tolidine takes place, producing an orange-colored reaction product. The colored zone 7 produced thereby extends from the beginning of the indicator layer 4 at the contact surface to the porous retainer element 5 in the direction toward the opening 8 of the diffusion tube. The length of the colored zone 7 is proportional to the amount of chlorine released and thus proportional to the quantity of trichloroethene diffused into the glass tube during measurement; this quantity, in turn, is proportional to the product of the trichloroethene concentration in the ambient air and the length of time taken for drawing the sample.

Accordingly, the diffusion testing tube can be calibrated directly as a product of part per million and hour (ppm×h) trichloroethene, so that to determine the mean concentration, it is only necessary to read off the indication provided by the colored zone 7 in ppm×h and then divide the same by the sampling time in hours.

To perform a trichloroethene measurement, the porous plug 3 is a woven fabric of steel, for instance, and the indicator layer 4 is inert quartz with a grain size of from 0.8 to 1 mm impregnated with o-tolidine at a concentration of 0.001%. The porous retainer element 5 is made of ceramic, and the reagent layer 6 is silica gel having a grain size of 0.6 to 0.8 mm, which is impregnated with chromium (VI) oxide at a concentration of 5% and concentrated sulfuric acid at a concentration of 25%.

It is understood that the foregoing description is that of the preferred embodiments of the invention and that various changes and modifications may be made thereto without departing from the spirit and scope of the invention as defined in the appended claims.

What is claimed is:

1. A colorimetric gas-diffusion testing tube for detecting a particular gas comprising:
   a testing tube closed at both ends and having an end portion and a main portion;
   said testing tube having a tube wall configured so as to be weakened at only a predetermined location thereon so as to permit only said end portion to be separated from said main portion so as to cause the latter to have only a single opening for receiving said particular gas into said main portion when said end portion is separated from the latter;
   a porous reagent layer disposed in said main portion between the closed end thereof and said predetermined location;
   an indicator layer inert to said particular gas to be detected and mounted between said predetermined location and said porous reagent layer for conducting said particular gas to said porous reagent layer; and,
   said porous reagent layer being for converting said particular gas into substances for coloring said indicator layer as said substances migrate into the latter.

2. The colorimetric gas-diffusion testing tube of claim 1, further comprising a second indicator layer disposed in said testing tube; and, a porous holding member for partitioning said second indicator layer from said porous reagent layer.

3. The colorimetric gas-diffusion testing tube of claim 1, further comprising: a porous plug disposed between said opening and said indicator layer for partitioning off the latter from said predetermined location; and, a porous holding member for partitioning off said indicator layer from said porous reagent layer.

4. The colorimetric gas-diffusion testing tube of claim 1, wherein said porous reagent layer and said indicator layer both have a carrier made of granular inert material.

5. The colorimetric gas-diffusion testing tube of claim 4, wherein said granular material is comprised of quartz.

6. The colorimetric gas-diffusion testing tube of claim 1, said tube wall having a reduced thickness at said predetermined location thereby permitting said end portion to be separable from said main portion.

7. A colorimetric gas-diffusion testing tube for detecting a particular gas comprising:
   a testing tube closed at both ends and having an end portion and a main portion;
   said testing tube having a tube wall configured so as to be weakened at only a predetermined location thereon so as to permit only said end portion to be separated from said main portion so as to cause the latter to have only a single opening for receiving said particular gas into said main portion when said end portion is separated from the latter;
   a porous reagent layer disposed in said main portion between the closed end thereof and said predetermined location;
   an indicator layer inert to said particular gas to be detected and mounted between said predetermined location and said porous reagent layer for conducting said particular gas to said porous reagent layer;
   said porous reagent layer being for converting said particular gas into substances for coloring said indicator layer as said substances migrate into the latter; and
   said porous reagent layer having a carrier impregnated with chromium (VI) oxide and sulfuric acid and said indicator layer having a carrier impregnated with o-tolidine.

* * * * *